United States Patent
Gerald, II et al.

(10) Patent No.: US 7,737,691 B2
(45) Date of Patent: *Jun. 15, 2010

(54) NMR CHARACTERIZATION OF THIN FILMS

(75) Inventors: Rex E. Gerald, II, Brookfield, IL (US);
Robert J. Klingler, Glenview, IL (US);
Jerome W. Rathke, Homer Glen, IL (US); Rocio Diaz, Chicago, IL (US);
Lela Vukovic, Westchester, IL (US)

(73) Assignee: The University of Chicago, Chicago, IL (US)

( * ) Notice: Subject to any disclaimer, the term of this patent is extended or adjusted under 35 U.S.C. 154(b) by 2 days.

This patent is subject to a terminal disclaimer.

(21) Appl. No.: 12/198,724

(22) Filed: Aug. 26, 2008

(65) Prior Publication Data

US 2008/0309337 A1    Dec. 18, 2008

Related U.S. Application Data

(63) Continuation of application No. 11/484,348, filed on Jul. 11, 2006, now Pat. No. 7,456,630.

(60) Provisional application No. 60/719,479, filed on Sep. 22, 2005.

(51) Int. Cl.
*G01V 3/00* (2006.01)

(52) U.S. Cl. .................................................. 324/307

(58) Field of Classification Search ......... 324/300–322;
600/410–435
See application file for complete search history.

(56) References Cited

U.S. PATENT DOCUMENTS

| | | | | |
|---|---|---|---|---|
| 4,101,925 A * | 7/1978 | Kelley et al. | ................. | 257/741 |
| 5,572,125 A * | 11/1996 | Dunkel | ....................... | 324/307 |
| 5,592,083 A * | 1/1997 | Magnuson et al. | .......... | 324/300 |
| 5,754,048 A * | 5/1998 | Bielecki | ..................... | 324/321 |
| 6,118,274 A * | 9/2000 | Roffmann et al. | ........... | 324/321 |
| 6,194,898 B1 * | 2/2001 | Magnuson et al. | .......... | 324/300 |
| 6,720,769 B2 * | 4/2004 | Gerald et al. | ............... | 324/318 |
| 6,806,713 B2 * | 10/2004 | Wong | .......................... | 324/318 |
| 6,865,408 B1 * | 3/2005 | Abbink et al. | .............. | 600/310 |
| 6,881,363 B2 * | 4/2005 | Carlson et al. | ................ | 506/37 |
| 6,958,608 B2 * | 10/2005 | Takagi et al. | ................ | 324/318 |
| 7,013,709 B2 * | 3/2006 | Hajduk et al. | .................. | 73/37 |
| 7,151,374 B2 * | 12/2006 | Doty | ........................... | 324/321 |
| 7,164,269 B2 * | 1/2007 | Hasegawa et al. | ........... | 324/318 |
| 7,173,424 B2 * | 2/2007 | Saitoh et al. | ................ | 324/318 |
| 7,199,581 B2 * | 4/2007 | Corver et al. | ............... | 324/308 |
| 7,217,542 B2 * | 5/2007 | Tyvoll et al. | ............... | 435/91.1 |
| 7,456,630 B2 * | 11/2008 | Gerald et al. | ............... | 324/307 |
| 2007/0196589 A1 * | 8/2007 | Fu et al. | ..................... | 427/512 |

* cited by examiner

*Primary Examiner*—Brij B Shrivastav
*Assistant Examiner*—Dixomara Vargas
(74) *Attorney, Agent, or Firm*—Foley & Lardner LLP

(57) ABSTRACT

A method, apparatus, and system for characterizing thin film materials. The method, apparatus, and system includes a container for receiving a starting material, applying a gravitational force, a magnetic force, and an electric force or combinations thereof to at least the starting material, forming a thin film material, sensing an NMR signal from the thin film material and analyzing the NMR signal to characterize the thin film of material.

19 Claims, 12 Drawing Sheets m (PEG)=13.2 mg, Film Thickness ~ 0.1 mm

NMR CHARACTERIZATION OF THIN FILMS

CROSS-REFERENCE TO RELATED PATENT APPLICATIONS

This application is a continuation and claims priority from copending U.S. patent application Ser. No. 11/484,348, filed Jul. 11, 2006, which claims priority from U.S. Provisional Patent Application Ser. No. 60/719,479, filed Sep. 22, 2005.

GOVERNMENT INTEREST

The United States Government has certain rights in the invention pursuant to Contract No. W-31-109-ENG-38 between the U.S. Department of Energy and the University of Chicago operating Argonne National Laboratory.

The present invention is related generally to use of nuclear magnetic-resonance (NMR) to characterize thin films. In particular, thin films prepared by use of molecule subcomponents result in tailored films which can benefit from careful control of the assembly process by use of NMR spectroscopy and imaging.

BACKGROUND OF THE INVENTION

The tailored assembly of molecules by use of new methods, such as application of gravitational, magnetic and electric field forces can result in whole new classes of thin films with a variety of important uses. Thus, it is important to be able to characterize the starting components, intermediate and final components, as well as location of molecular assemblages on the substrate; but virtually no methods allow adequate characterization of such assemblages, especially throughout the complex process of fabrication. Moreover, there is a substantial need for comparison of theoretical model assemblies with actual experimental data so as to control and characterize thin film structures generally.

SUMMARY OF THE INVENTION

NMR spectroscopy and imaging is used to carry out detailed chemical and macroscopic structural characterization of thin films. In one system a cylindrical device allows receiving a starting layer of molecules which can be characterized and compared with theoretical NMR spectra. Throughout the process of assembling molecules in a layer, the NMR method can be used to carry out such comparisons with theory as well as perform fundamental chemical characterization, film thickness measurements, and evaluate other macroscopic features, such as characterizing the layering of different chemical components and obtaining dynamical information about the chemical and molecular constituents. Consequently, NMR can perform characterization of the materials and also enable control of the preparation of a desired film product.

Various aspects, features and advantages of the invention as described hereinafter, and these and other improvements will be described in more detail below, including the drawings as described below.

DETAILED DESCRIPTION OF THE PREFERRED EMBODIMENTS

A method of thin film characterization involving NMR spectroscopy can be used to perform measurements heretofore unavailable. In preparation of thin films, such as the development of the tailoring of molecular assemblages, it has become necessary to control aspects of preparation. Such features include tailoring as well as characterization of starting, intermediate and finished product chemical features, including macroscopic aspects such as film thickness, orientation, and the location of particular film components in space.

Figure 1:
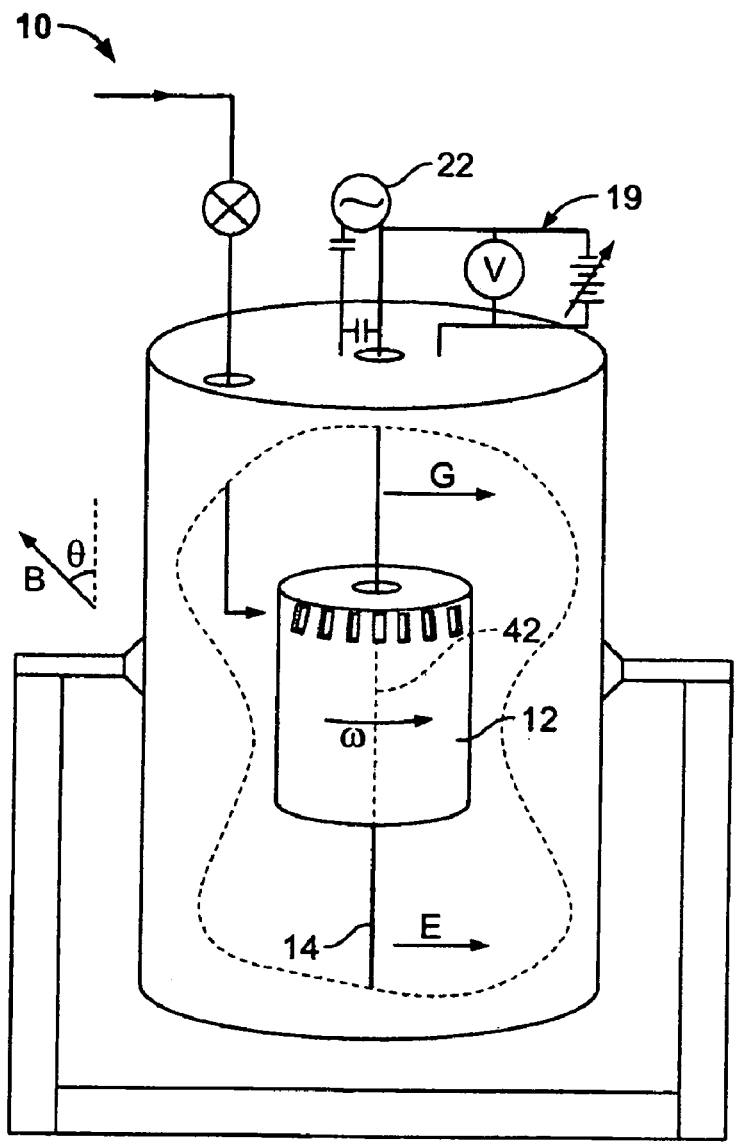
FIG. 1 illustrates an example of a device for preparation and NMR analysis of a tailored thin film.

Using the example device 10 shown in FIG. 1, the method of characterization of the products of the method and apparatus can be illustrated. The device 10 is, of course, only one example of use for film preparation; and the method and system described herein is applicable to any film for which characterization is sought. In the device 10 of FIG. 1 a gravitational field force, G; magnetic field force, B; and electric field force, E, are shown. Note that the E field force can be parallel or perpendicular (or combinations thereof) to a rotor axis 14 (denoted central axis conductor 42 within the spinning cylinder 12 as in FIG. 1 and FIG. 8). A radial electric field E is generated by power source 19. The G field force can perform separations as well by molecule mass, such as for films with slightly different density. We can therefore, for example, fabricate a film with holes and then put molecules through the holes in the film because of the separability of different densities and/or of different sizes of molecules which can be inserted there through.

Figure 2A:
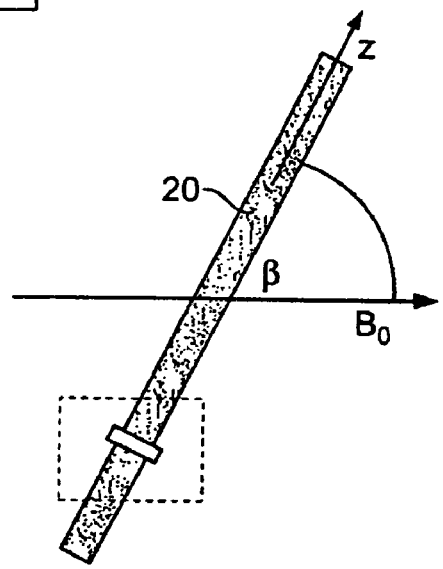
FIG. 2A illustrates a thin cylinder film and inclined magnetic field.
Figure 2B:
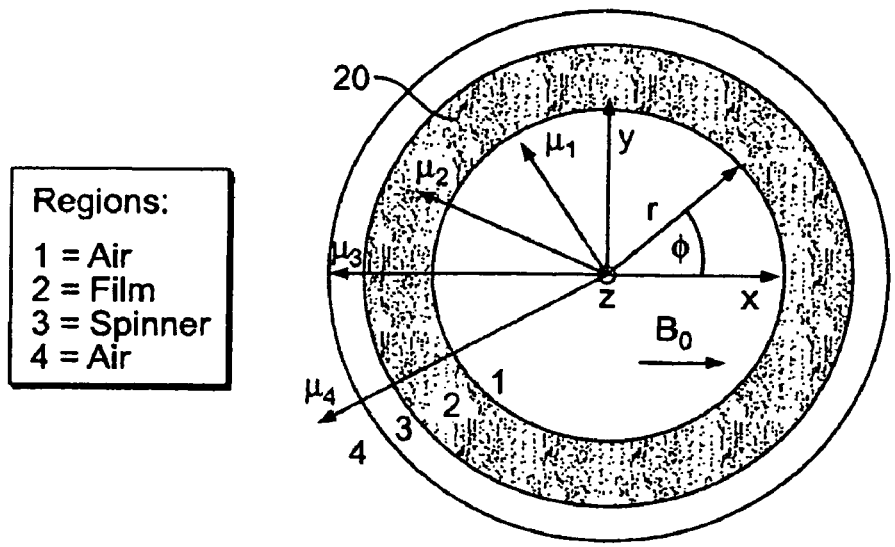
FIG. 2B illustrates a cylindrical shell cross-section and FIG. 2C illustrates a chemical shift NMR spectrum for a thin film on a cylinder.
Figure 2C:
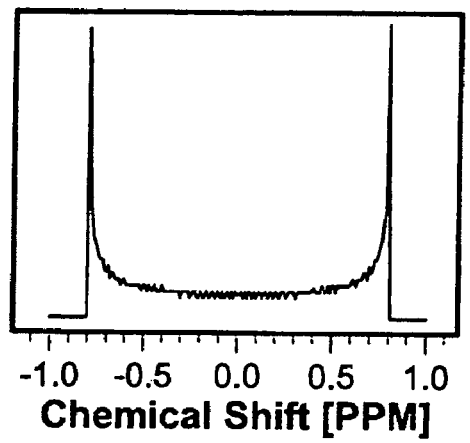

FIG. 2A illustrates a thin cylinder film with long axis Z inclined at an angle $\beta$ with respect to magnetic field $B_0$. FIG. 2B illustrates the cross-section of a cylindrical film 20 with labels indicating permeabilities ($\mu$) for spinning cylinder 12 ($\mu_3$), cylindrical film 20 ($\mu_2$), and interior ($\mu_1$) and exterior ($\mu_4$) air regions. FIG. 2C illustrates a chemical shift NMR spectrum for the thin film 20 on the interior of cylinder 12.

As shown in FIGS. 3A-3F, the environmental ("chemical") shift of the NMR resonance depends on the permeability ($\mu$) of the thin film 20, the material that surrounds the film 20, and on the macroscopic geometry of the film 20 with the NMR peak shape (obtained using NMR device 22) containing information about how the induced magnetic field changes with angle $\emptyset$, angle $\beta$, permeabilities ($\mu$) and nuclear shielding parameters ($\sigma$):

$$B_{ind} = B_0 \cdot \left\{ 1 - \frac{1}{2}(\mu_2 - \mu_4) - \frac{a_2^2}{2r^2}(\mu_2 - \mu_1)\cos 2\phi \right\} \cdot \quad \text{Eqn. (1)}$$
$$\left\{ 1 - \left[ (\sigma_{xx} - \sigma_i)\cos^2\phi + (\sigma_{yy} - \sigma_i)\sin^2\phi + \left(\frac{\sigma_{xy} + \sigma_{yx}}{2}\right)\sin 2\phi \right] \right\} \cdot \cos^2\beta$$

Figure 3A:
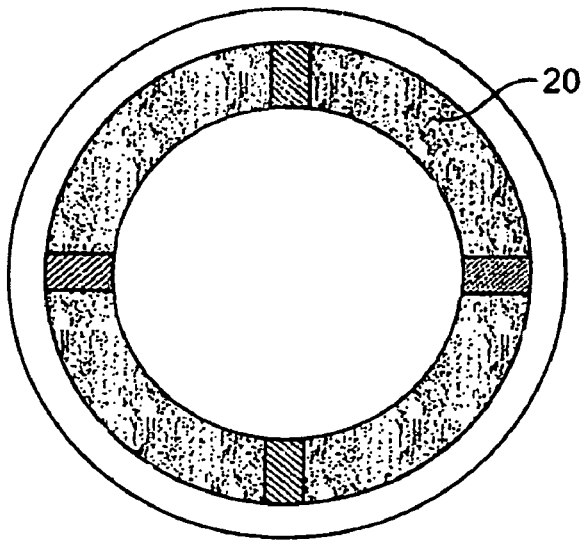
FIG. 3A illustrates a cylindrical cross-section of a thin film with differing local magnetic environments for the same chemical constituents around the cross section.
Figure 3B:
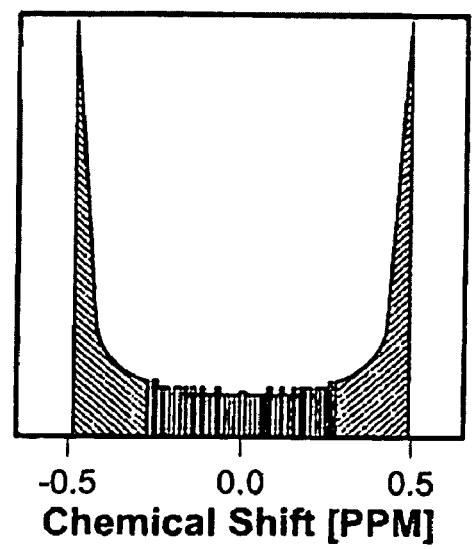
FIG. 3B shows an NMR spectrum with different chemical shifts for the same chemical constituents being separable.
Figure 3C:
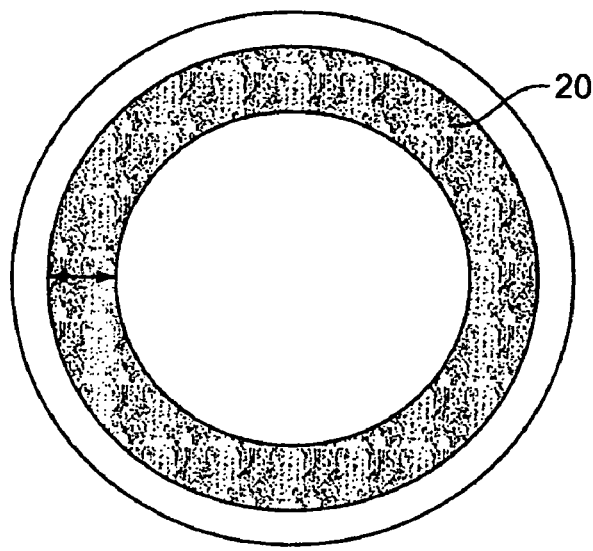
FIG. 3C illustrates the thickness of a manufactured film.
Figure 3D:
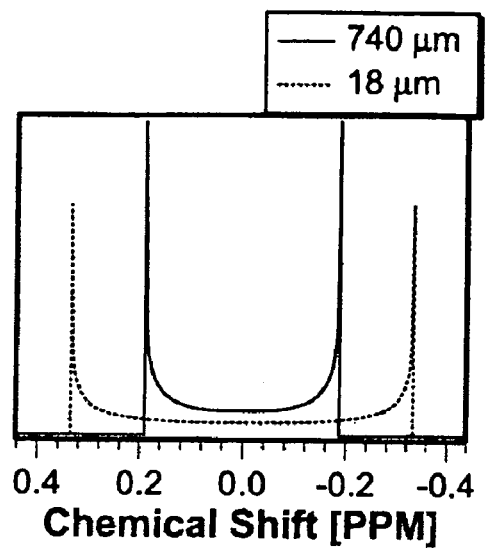
FIG. 3D shows two different NMR spectra corresponding to two films having different thickness.
Figure 3E:
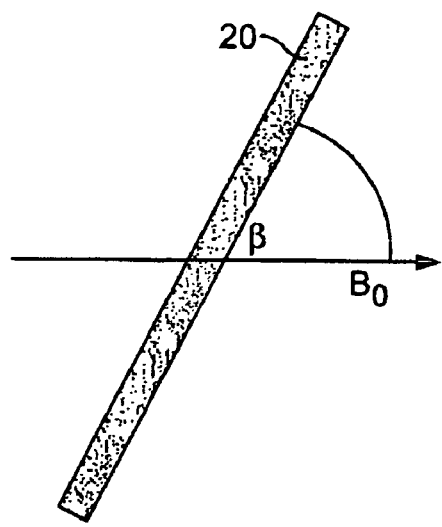
FIG. 3E shows application of a magnetic field at an angle to a thin film.
Figure 3F:
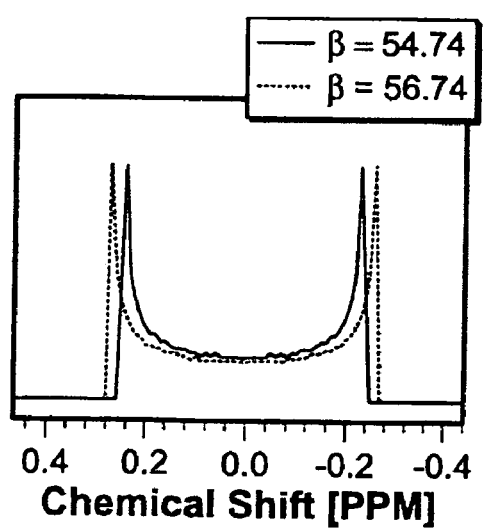
FIG. 3F shows comparative NMR spectra for two different angles of magnetic field incidence.

As further noted in FIG. 3B, the NMR peak shape can include information about the local magnetic environment with one environment separating to one side of the spectrum versus the other environments. In addition, the peak separation between the two NMR peaks of FIG. 3B provides information about the thickness of the cylindrical shell of the film 20 (see FIGS. 3C-3D). In addition, the separation provides information about the angle between $B_o$ and the principal rotor axis 14 of the cylinder of the device 10 (see FIGS. 3E-3F).

Figure 4A:
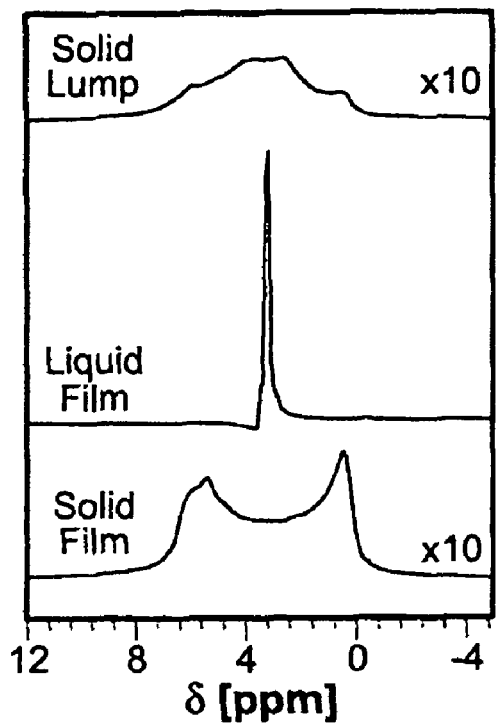
FIG. 4A shows a series of NMR spectra for different spinning conditions of the cylinder of FIG. 1.
Figure 4B:
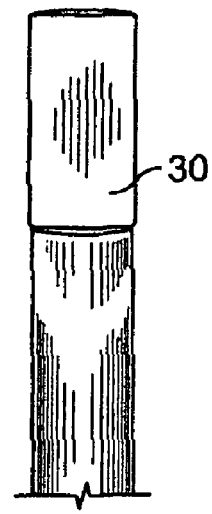
FIG. 4B illustrates a free-standing cylinder support film disposed on an extraction rod with a front perspective view of the film removed from the cylinder.
Figure 4C:
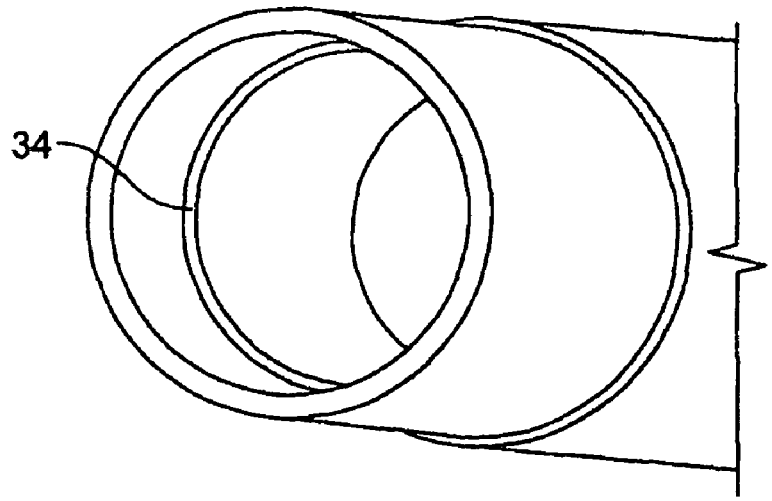
FIG. 4C illustrates a polyethylene glycol (PEG) film disposed on an inner surface of the cylinder.

FIGS. 4A-4C show the accompanying NMR spectra associated with the state of manufacture and an end product film 30. In the state when the material is deposed on a cylinder 12 of the device 10, but is not being spun, the static spectrum is an irregular, broad peak. After spinning at a preferred, "magic angle" (54.7°; v=2.9 kHz and T=341 K), the liquid film has a sharp NMR peak. After spinning is stopped, and the end product film 30 has solidified, the spectrum establishes a broad twin peak characteristic of a particular thickness and orientation of the final end product film 30.

Further, the device 10 of FIG. 1 can be used to obtain films from compounds that are soft and waxy at room temperature. The existing device 10 enables stable spinning at frequencies between 1 and 4 kHz, during which compounds inside the spinning cylinder 12 are pushed by the gravitational force onto the walls of the cylinder 12. The centrifugal force reshapes compounds into thin cylindrical shells, i.e., thin classic film product (see film 34 in FIG. 4C). When the device 10 is placed inside the NMR apparatus, the features of the thin classic film product 34 can easily be analyzed, while it is spinning at high and low speeds and upon shutting the spinning off. High resolution NMR spectra of the end product film 34 formed within the device 10 under conditions of magic angle spinning (MAS) do not provide orientational information of the component molecules, but these spectra are useful for compound identification, obtaining proper spin counts, and establishing whether there are impurities in the film product 34. As the spinning of the cylinder 12 is turned off, the static spectra that provide molecular orientation information can be obtained. Slow spinning of the cylinder 12 is also useful for characterizing the thickness, shape, and orientation of the end film product 34.

In the context of a molecule nanoweaver methodology, the term "classic film" refers to a film in which molecules do not have preferential orientations; the component molecules that make up a film assume all possible orientations since they tumble isotropically at elevated temperatures before they are locked in random positions upon cooling. The lineshape in the static NMR spectrum of a classic film is due to the shape of the sample. Thus, by knowing only the geometrical shape of the sample container (e.g., the cylinder 12), a theoretical model can be used to predict the lineshape. In a theoretical model (see Eqn. 1), the lineshape due to the shape of the sample is scaled by the term that is related to the thickness of the end film product 34. In order to compare the theoretical lineshape to the experimental results, the lineshape is also scaled by the magnetic susceptibility of the compound used in the experiment (see FIGS. 2A-2C and Eqn. 1).

Figure 5A:
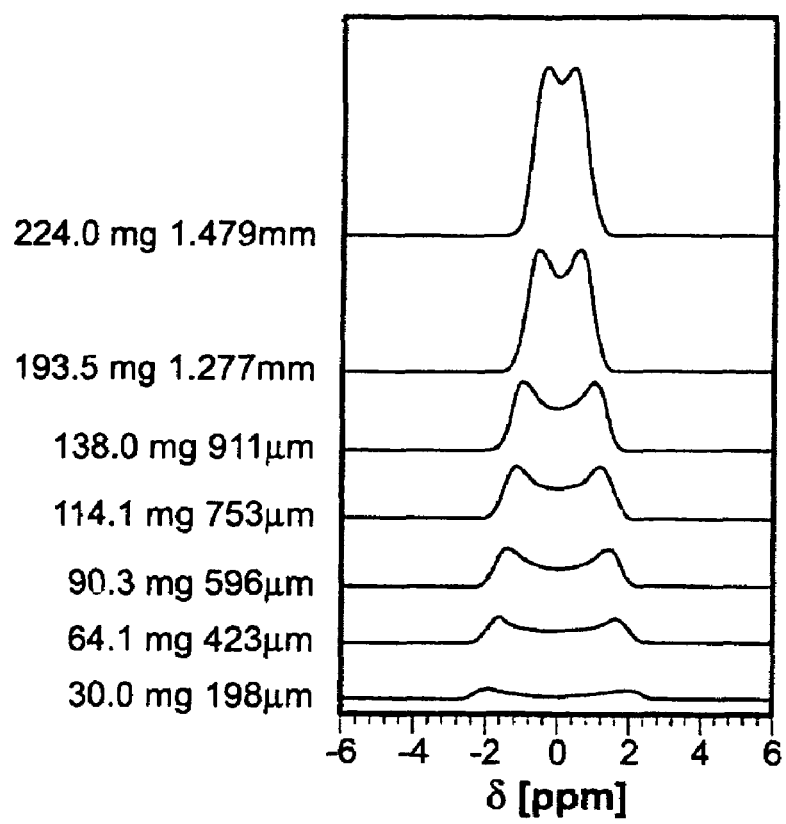
FIG. 5A shows simulated NMR spectra for nonadecane of various film thicknesses and FIG. 5B shows experimental NMR spectra compared to the simulated results.
Figure 5B:
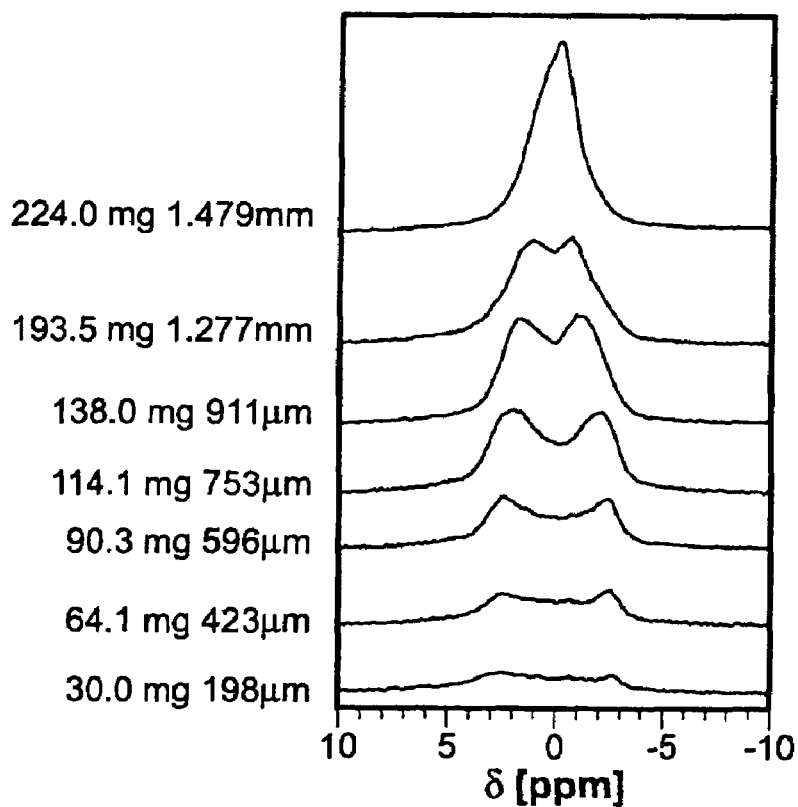

The theoretical model predicts that the static film product 34 obtained inside the cylinder 12, has a characteristic lineshape that is a doublet whose center is at the isotropic value of the chemical shift for the specific compound. Theoretical lineshapes for nonadecane films shown in FIG. 5A have been scaled by the film thickness parameter and molecular parameters that relate to the magnetic susceptibility of nonadecane. To see if the theoretical lineshapes, based on the geometric factor, agree with experimental results, several nonadecane films of different thicknesses were prepared and studied. Theoretically predicted and experimentally obtained lineshapes for nonadecane films are shown in FIGS. 5A and 5B, respectively. The substantial agreement between theory and experiment is clear, and this indicates that created end film products 34 are classic films. Yet, in FIGS. 5A and 5B the experimental and theoretical lineshapes for nonadecane films differ slightly in magnitudes of the splittings. The splitting is a distance (in ppm) between two peaks that make up a doublet. In calculations, values of film thickness are calculated from mass and density of the nonadecane placed inside the spinner, and the magnetic susceptibility parameter is experimentally determined. Since these scaling values have errors associated with them, the theoretical splittings are affected by these errors.

Equations used in obtaining the theoretical lineshapes for nonadecane films of FIG. 5A are based on geometric shapes of thin films (see FIG. 2A). Yet, these equations can be modified to include molecular effects. Molecular information is contained in the components of the molecular shielding tensor. The shielding tensor components contribute to the peak lineshape in the situation when molecules have preferential orientations, which occur when molecules are ordered on the nanometer scale. We expect that as the process of building the molecule nanoweaver device 10 is completed and experiments are performed with the purpose of obtaining films with molecules ordered on the nanometer scale, then theoretical calculations will become crucial in the analysis of the experimentally obtained lineshapes. Such analysis can be performed using computer systems 53 (see FIG. 8) with computer software modules to perform the appropriate mathematical analysis.

Figure 8:
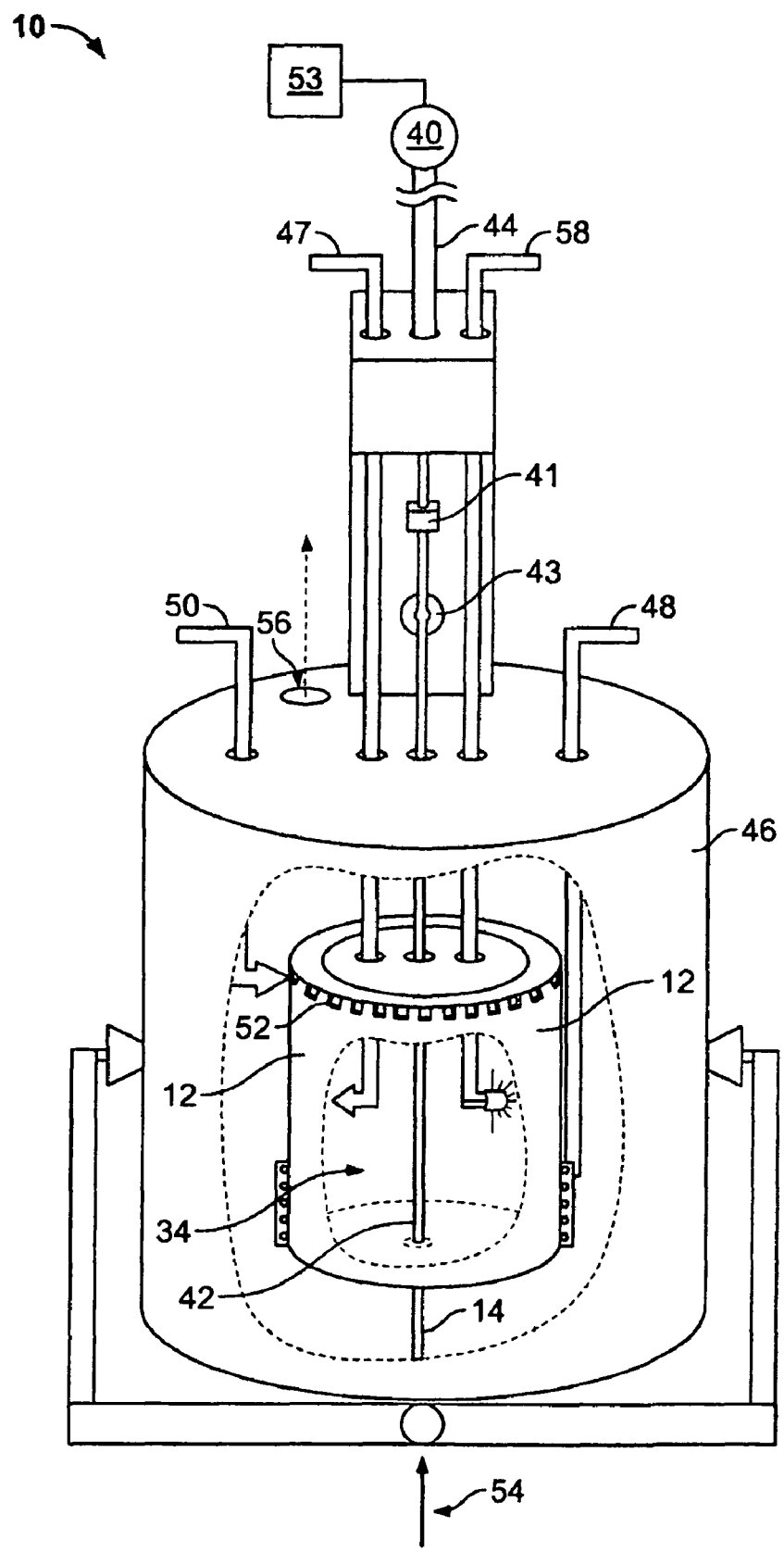
FIG. 8 illustrate a form of the device of FIG. 1 but including various detectors for monitoring film formation.

In addition to high resolution spectra and static NMR spectra, unique information about prepared isotropic classic film product 34 can be deposited and processed by use of the toroid cavity detector (TCD) NMR spectrometer 40 (see FIG. 8). The device 10 includes an outer housing 46, a monomer source 47, a bearing gas 48 for supporting the spinning cylinder 12, and a drive gas 50 for pushing against drive fins 52 of the cylinder 12. Also included is heating/cooling gas 54, a vent 56 and a direct viewing device in the form of fiber optic cable 58 to view film formation and irradiate film with UV/VIS/IR light.

The spinning cylinder 12 of the device 10 is, with the film product 34 cast on its inside walls inside the toroid cavity housing 46, disposed so that the central axis conductor 42 of the cylinder 12 coincides with central conduit 44 that is connected to the TCD NMR spectrometer 40. Ceramic capacitor 41, variable capacitor 43, central axis conductor 42, and the housing 46 comprise a radiofrequency tunable resonant circuit useful for recording TCD NMR images. Resulting TCD NMR images are three-dimensional, with chemical shift, radial, and intensity dimensions (see, for example, FIGS. 9A-9C described below). Thus, the TCD NMR spectrometer 40 gives normal NMR spectra of compounds observed along the chemical shift axis. In addition, the radial information in the second dimension indicates how far away from the central axis conductor 42 the compound identified from the information along the chemical shift is located. The TCD NMR spectrometer 40 can thus be used to study multilayered classic films.

Figure 6A:
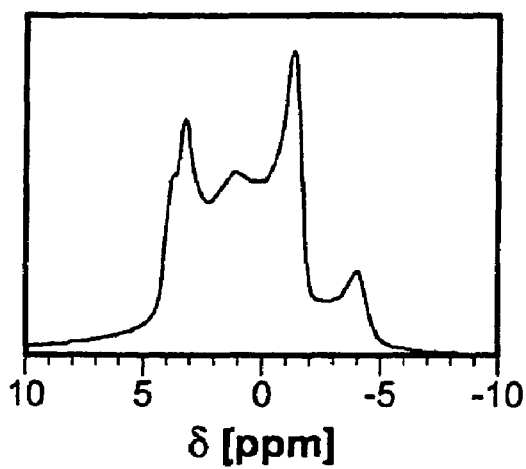
FIG. 6A shows a static NMR spectrum of a film after spinning in the cylinder of FIG. 1 for a mixture of nonadecane and PEG.
Figure 6B:
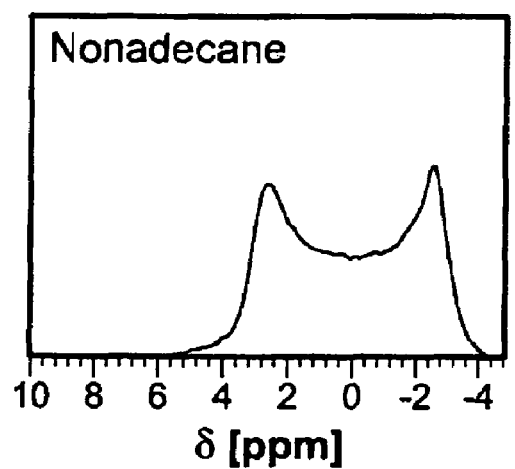
FIG. 6B shows an experimental NMR spectrum for a nonadecane film.
Figure 6C:
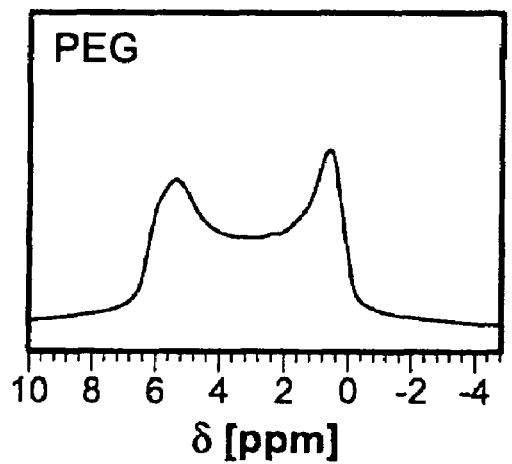
FIG. 6C shows an experimental NMR spectrum for a PEG film.
Figure 6D:
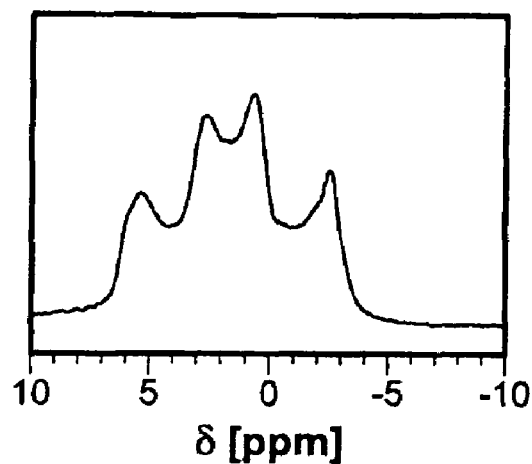
FIG. 6D shows a scaled 50:50 sum NMR spectrum of a film of nonadecane and PEG.
Figure 6E:
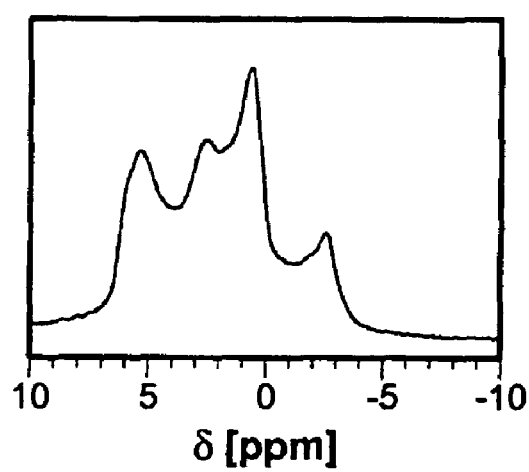
FIG. 6E shows a 30:70 sum NMR spectrum of a film of nonadecane and PEG.
Figure 7A:
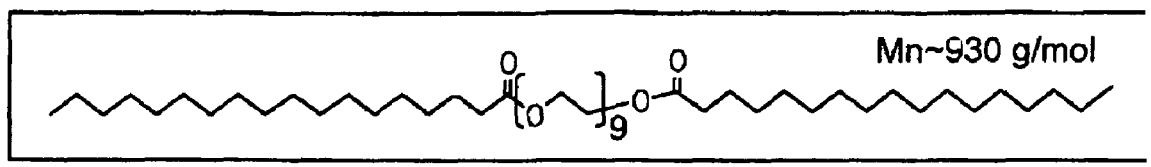
FIG. 7A shows a schematic of a PEG-distearate molecule.
Figure 7B:
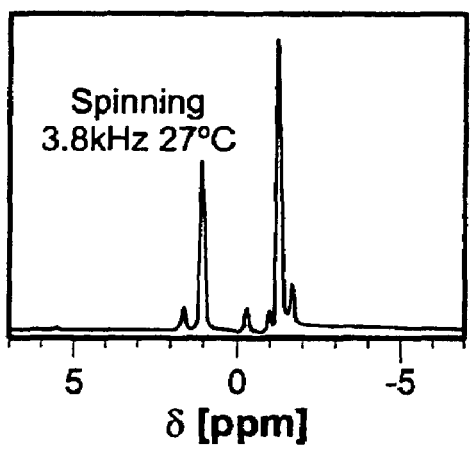
FIG. 7B shows a magic angle spinning (MAS) NMR spectrum for PEG-distearate.
Figure 7C:
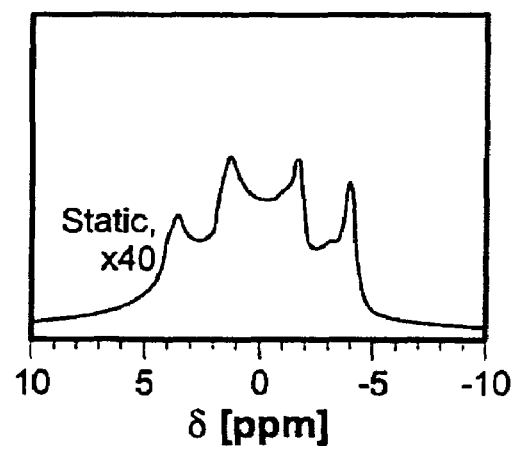
FIG. 7C shows a static NMR spectrum for of a film of PEG-distearate.
Figure 7D:
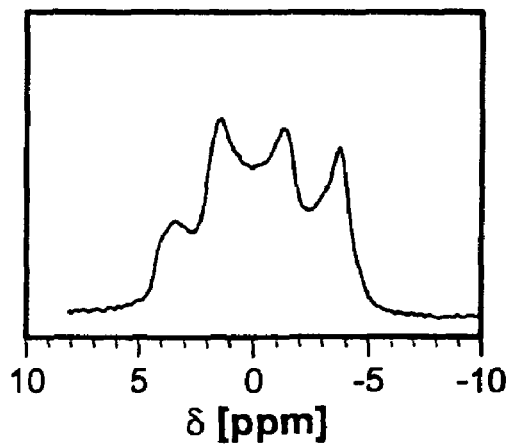
FIG. 7D shows a simulation NMR spectrum of a film from adding scaled static NMR spectra of methylene groups from nonadecane and PEG films.
Figure 7E:
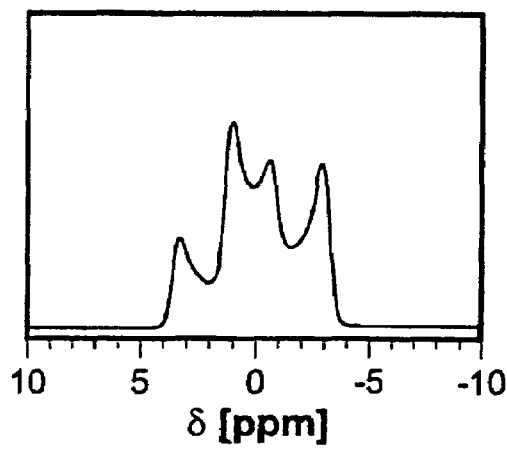
FIG. 7E shows a simulated static NMR spectrum of a film obtained from a theoretical expression of the induced magnetic field, $B_{ind}$.

In FIGS. 6A-6E is shown the characterization of a two-layer film composed of nonadecane (31.9 mg) and polyethylene glycol (PEG) (39.9 mg) which are introduced into the device 10 by the monomer source 47 or by alternate means. The resulting multilayer film 34 can be characterized by measurement of the NMR spectrum and comparing with the NMR spectrum of each constituent of the film 34. FIG. 6A shows the recorded H-NMR spectrum of a two-layer film composed of an equal mole mixture of nonadecane (31.9 mg) and PEG (39.9 mg). FIG. 6B shows the recorded H-NMR spectrum of a film of nonadecane (31.9 mg). FIG. 6C shows the H-NMR spectrum of a film of PEG (39.9 mg). Various combined spectra are shown. The spectrum in FIG. 6D is the scaled sum, composed of a 1:1 ratio (also denoted 50:50), of the nonadecane spectrum of FIG. 6B and the PEG spectrum of FIG. 6C. The spectrum in FIG. 6E is the scaled sum, composed of a 1:2.33 ratio (also denoted 30:70), of the nonadecane spectrum of FIG. 6B and the PEG spectrum of FIG. 6C. If the measured H-NMR spectrum is not simply the sum of the two individual spectra, then some molecular change or component loss has occurred. In FIGS. 7A-7E, experimental and simulation data for PEG-distearate illustrate further the deviation from identity and the substantial difference of the H-NMR spectrum when the cylinder 12 of the device 10 is spinning (see FIG. 7B) versus static (see FIG. 7C); the experimental static spectrum is compared to simulation results in FIGS. 7D and 7E. The simulated static H-NMR spectrum shown in FIG. 7D was composed of a ratio, determined by the number of methylene protons in the alkane and polyethylene oxide (PEO) chains in the PEG-distearate molecule, of the nonadecane spectrum of FIG. 6B and the PEG spectrum of FIG. 6C. The simulated static spectrum shown in FIG. 7E was composed of a ratio, determined by the number of methylene protons in the alkane and PEO chains in the PEG-distearate molecule, of two spectra of the form shown in FIG. 2C (displaced from each other by the chemical shift difference between the methylene protons in the alkane and PEO chains) calculated using Equation (1).

Figure 9A:
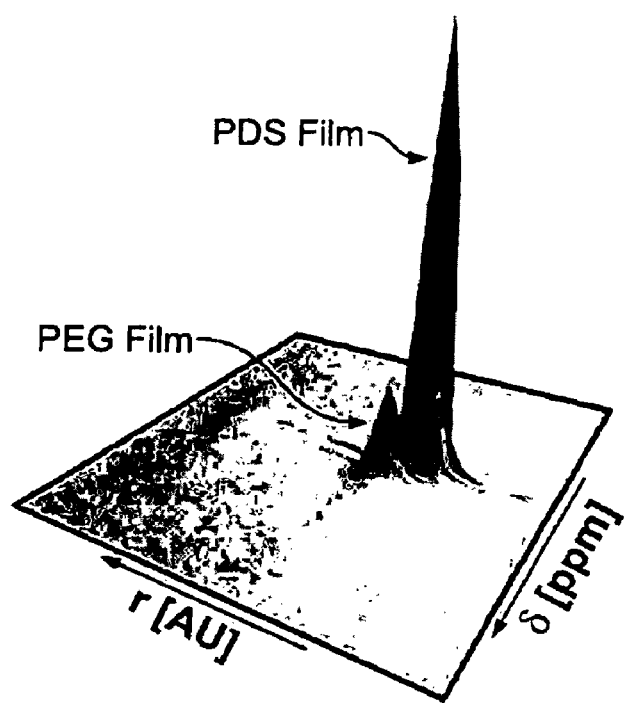
FIG. 9A illustrates a double-layered polydimethyl siloxane (PDS) and PEG film shown as topographical thickness at a particular radial position of a layer disposed on a cylinder.

One of the prepared films studied by TCD NMR spectrometer 40 contained polyethylene glycol (PEG) and polydimethyl siloxane (PDS). The TCD H-NMR image in FIG. 9A shows that PDS and PEG are macroscopically separated, since the peaks identifying each compound occur at different radial positions. In the prepared film 34 the outer layer is PEG, and the inner one is PDS. This separation of PEG from PDS was done by application of a centrifugal field force, and was due to the immiscibility and difference in density of the two compounds.

Figure 9B:
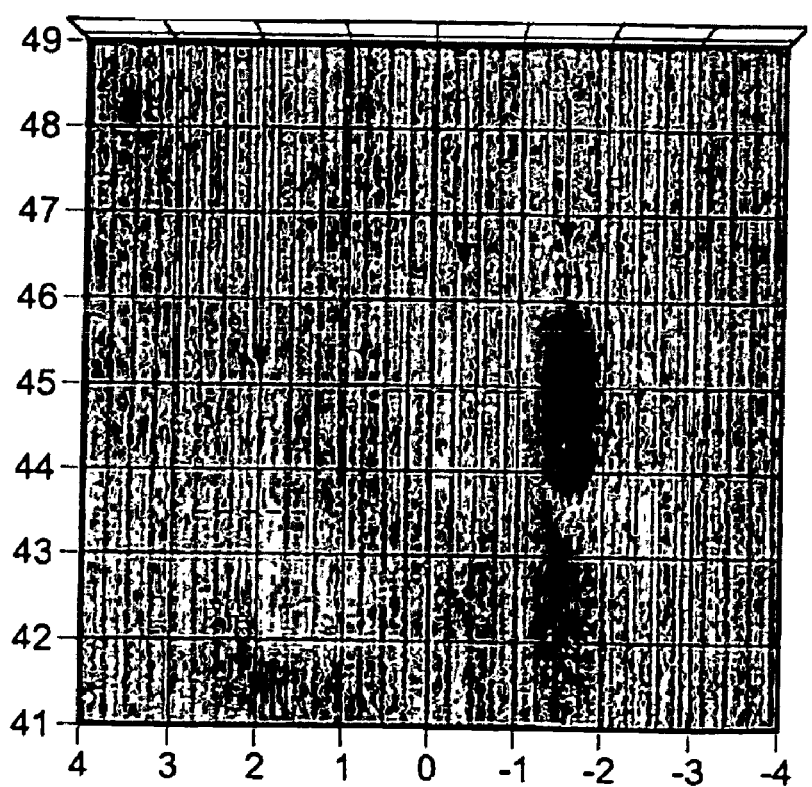
FIG. 9B illustrates a triple-layered film illustrated as a two-dimensional topograph.
Figure 9C:
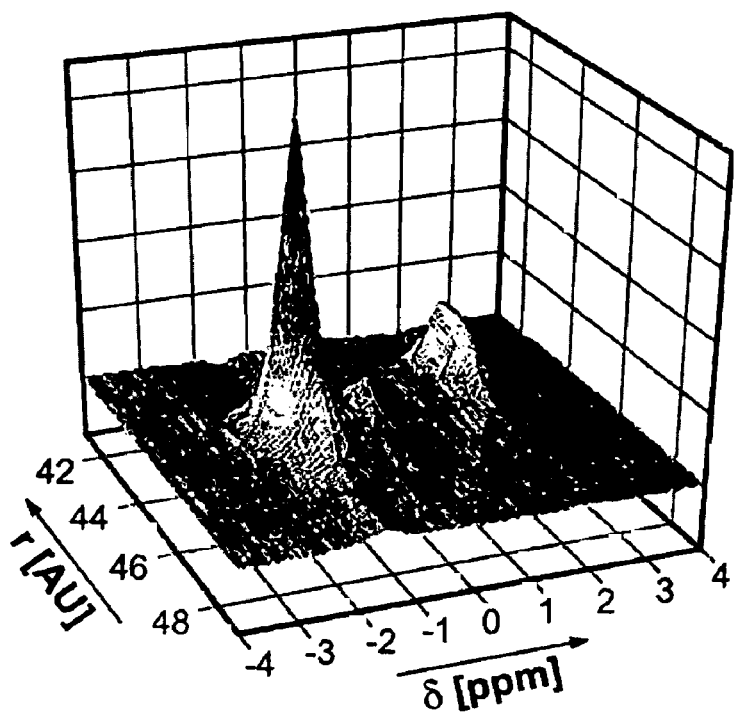
FIG. 9C illustrates the three-layer film as a three-dimensional topograph.

In another illustration of the invention, three compounds (PEG, PDS, and nonadecane) were used to prepare the classic film 34. The TCD H-NMR images of this system in FIGS. 9B-9C indicate that the resulting film 34 is composed of two layers, and further shows that the outside layer is PEG. FIGS. 9B-9C also show that the inside layer is a mixture of PDS and nonadecane. Thus, the TCD H-NMR results show that PDS and nonadecane are miscible with each other, but not with PEG. Units on the radial axis of FIGS. 9A-9C can be mathematically transformed in a known manner into real units of distance.

Figure 10A:
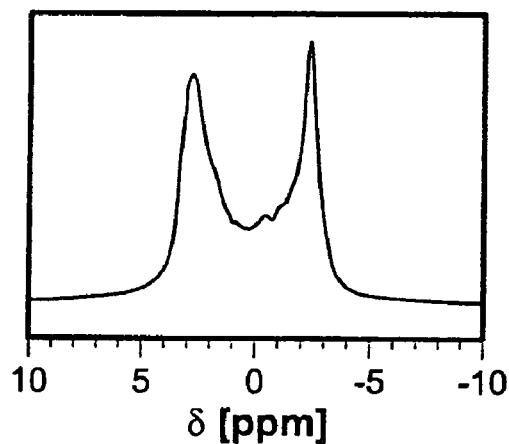
FIG. 10A illustrates a static NMR spectrum of a film taken after shut-down of cylinder spinning.
Figure 10B:
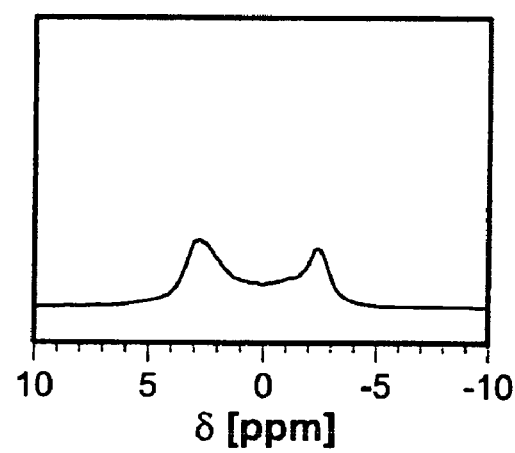
FIG. 10B shows the same material of FIG. 10A after a rheology relaxation time of 16 seconds.
Figure 10C:
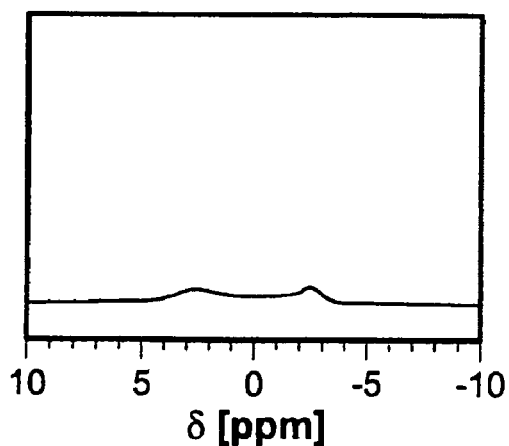
FIG. 10C illustrates the same material of FIG. 10A after a rheology relaxation time of 8.27 minutes.
Figure 11:
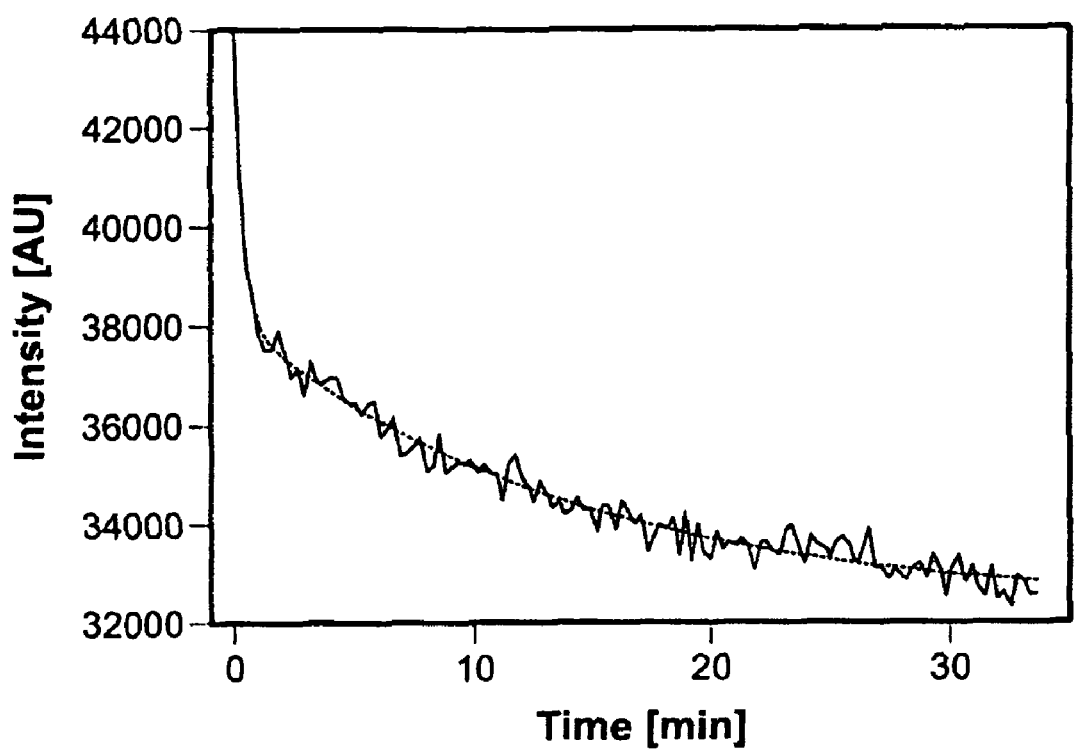
FIG. 11 illustrates a plot of the maximum NMR intensity as a function of rheology relaxation time after ceasing cylinder spinning.

FIGS. 10A-11 illustrate the dynamics of molecular assemblage and relaxation after spinning is stopped for the cylinder 12 of the device 10. The NMR spectrum at the end of the spinning (FIG. 10A) differs more and more as time passes (FIGS. 10B and 10C), which illustrate the mobility and configurational changes of the molecules that compose the thin film 34. FIG. 11 shows a graph of the peak maximum signal intensity of a series of H-NMR spectra of a typical nonadecane or PEG film 34, which includes data typified by the spectra shown in FIGS. 10A-10C, versus time in minutes. The curve was fit by the bi-exponential function: $y=y_0+ae^{-bx}+ce^{-dx}$. The parameters b and d describe two characteristic time constants that are associated with the dynamical processes of the molecules that compose the film 34, and that collectively are termed rheology relaxation parameters. The parameter b characterizes the faster relaxing component of the curve and ranges between 1 and 10 minute depending on the film 34, temperature and other factors; similarly, the parameter d characterizes the slower relaxing component of the curve and ranges between 50 minutes and 2 hours.

Figure 12:
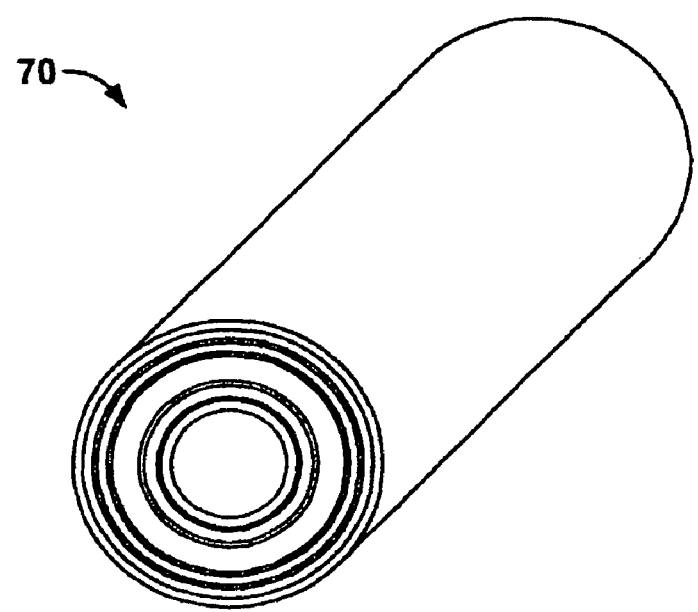
FIG. 12 shows a multilayer pharmaceutical in a cylinder shape.

FIG. 12 illustrates another application in the form of a multilayer capsule 70 which can be a time release geometry for pharmaceuticals. The different layer thicknesses can allow design of different time releases from very short to long duration. There can also be delay periods by having an inert layer disposed between active substance layers. Such a capsule geometry can readily be manufactured by the device 10 and designed and monitored by the methods of the invention described herein.

Figure 13:
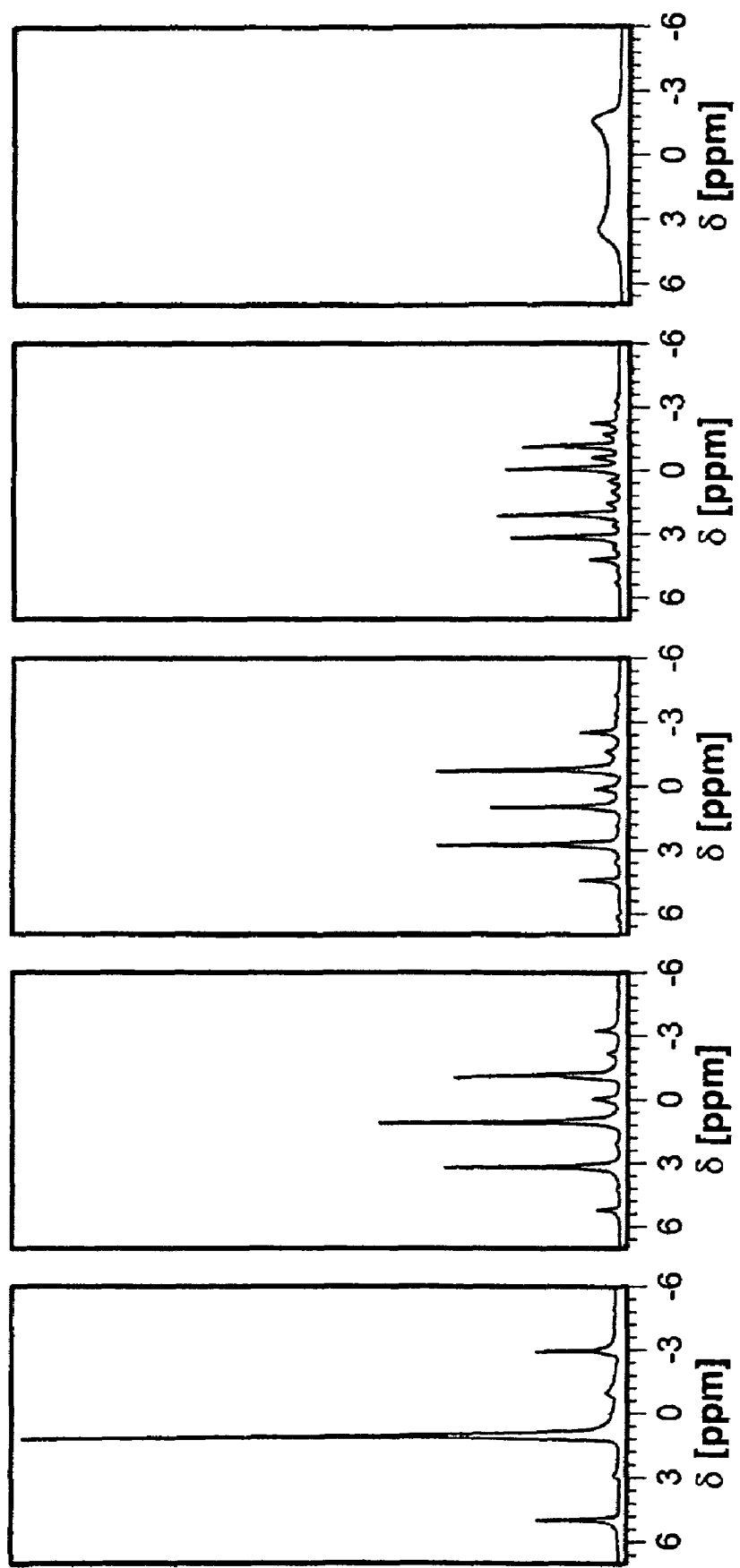
FIG. 13 shows a series of NMR spectra of a cylinder film spinning at different speeds.

FIG. 13 shows a series of NMR spectra of the cylindrical film 34 spinning at different speeds between 0 and approximately 1000 revolutions per second. The spinning axis, which is parallel to the central axis conductor 42, and the direction of the NMR magnetic field form an angle of 54.7°. The patterns of peaks in each NMR spectrum provide information that characterizes the morphology and orientation of the film. The method of spinning the cylinder film 34 at various angles (also known as off-magic angle spinning, or variable angle spinning) provides details of the film's structure and dynamics.

It should be understood that various changes and modifications referred to in the embodiment described herein would be apparent to those skilled in the art. Such changes and modifications can be made without departing from the spirit and scope of the present invention.

What is claimed is:

1. A method of characterizing a multi-layer thin film material, comprising:
   providing a plurality of starting materials;
   applying a gravitational force to at least the starting materials;
   heating and/or cooling the starting materials;
   forming a plurality of different layers of a thin film material comprising the plurality of starting materials;
   heating and/or cooling the thin film material;
   applying nuclear magnetic resonance (NMR) to the multi-layer thin film material using a device capable of obtaining an NMR signal having a radial component, a chemical shift component, and an intensity component characteristic of each of the plurality of different layers of the multi-layer thin film material; and
   analyzing the NMR signal in relation to at least one reference signal to evaluate one or more characteristics of any of the plurality of different layers of the multi-layer thin film material.

2. The method as defined in claim 1 wherein the step of analyzing the NMR signal comprises the step of comparing the NMR signal to selected theoretical models and experimental data.

3. The method as defined in claim 1 wherein the step of analyzing the NMR signal comprises the step of comparing the NMR signal to theoretical spectra.

4. The method as defined in claim 1 wherein the step of analyzing the NMR signal comprises the step of comparing a line shape of the NMR signal to theoretical models for different NMR peak shapes of different materials.

5. The method, as defined in claim 1 wherein the step of analyzing the NMR signal comprises the step of comparing the line shape of the NMR signal to theoretical models characteristic of known molecular effects.

6. The method as defined in claim 1 wherein the step of analyzing the NMR signal comprises the step of performing a chemical shift evaluation of the thin film material.

7. The method as defined in claim 1 wherein the step of analyzing the NMR signal comprises the step of determining local molecular magnetic environment of the thin film material.

8. The method as defined in claim 1 wherein the step of analyzing the NMR signal comprises the step of determining film thickness of the thin filth material by determining peak separation, in the NMR signal.

9. The method as defined in claim 1 further including the step of spinning the thin film material at a magic angle and analyzing the NMR signal to determine selected characteristics.

10. The method as defined in claim 9 wherein the step of analyzing comprises established chemical compound information for the thin film material.

11. The method as defined in claim 9 wherein the step of analyzing comprises obtaining proper spin counts for the thin film material.

12. The method as defined in claim 9 wherein the step of analyzing comprises establishing whether there are impurities in the thin film material.

13. The method as defined in claim 9 wherein the step of analyzing comprises evaluating static spectrum characteristic of molecular, orientation for the thin film material.

14. The method as defined in claim 1 wherein the step of applying a gravitational force comprises slow spinning of the thin film material for characterizing at least one of film thickness, film shape and orientation of the thin film material.

15. The method as defined in claim 1 wherein the thin film material is constructed of pre-programmed thickness layers and selected chemical compounds, 16. The method as defined in claim 1 further including the step of inserting a biologically active layer in the multi-layer thin film.

17. A method of characterizing a multi-layer thin film material, comprising:
    providing a plurality of starting materials;
    applying a gravitational force to at least the starting materials;
    heating and/or cooling the starting materials;
    forming a plurality of different layers of a thin film material comprising the plurality of starting materials;
    heating and/or cooling the thin film material;
    spinning the thin film material at a magic angle;
    applying, nuclear magnetic resonance (NMR) to the thin film material using a device capable of obtaining an NMR signal characteristic of the plurality of different layers of the thin film material; and
    analyzing the NMR signal in relation to at least one reference signal to determine selected characteristics of the thin film material selected from the group consisting of: established chemical compound information for the thin film material; obtaining proper spin counts for the thin film material; establishing whether there are impurities in the thin film material; and evaluating static spectrum characteristic of molecular orientation for the thin film material.

18. A method of characterizing a multi-layer thin material, comprising:
    providing a plurality of starting materials;
    applying a gravitational force to at least the starting materials;
    heating and/or cooling the starting materials;
    forming a plurality of different layers of a thin film material comprising the plurality of starting materials;
    heating and/or cooling the thin film material;
    applying nuclear magnetic resonance (NMR) to the thin film material using a device capable of obtaining an NMR signal characteristic of the plurality of different layers of the thin film material; and
    analyzing the NMR signal in relation to at least one reference signal to evaluate one or more characteristics of the thin film material,
    wherein the step of analyzing the NMR signal comprises the step of determining film thickness of the thin film material by determining peak separation in the NMR signal.

19. A method of characterizing a multi-layer thin film material, comprising:
    providing a plurality of starting materials;
    applying a gravitational force to at least the starting materials;

heating and/or cooling the starting materials;
forming a plurality of different layers of a thin film material comprising the plurality of starting materials; including a biologically active layer;
heating and/or cooling the thin film material;
applying nuclear magnetic resonance (NMR) to the thin film material using a device capable of obtaining an NMR signal characteristic of the plurality of different layers of the thin film material; and
analyzing the NMR signal in relation to at least one reference signal to evaluate one or more characteristics of the thin film material.

* * * * *